(12) United States Patent
Song

(10) Patent No.: US 10,849,589 B2
(45) Date of Patent: Dec. 1, 2020

(54) X-RAY IMAGING APPARATUS AND CONTROL METHOD THEREOF

(71) Applicant: Samsung Electronics Co., Ltd., Suwon-si (KR)

(72) Inventor: Sang Ha Song, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 210 days.

(21) Appl. No.: 15/870,409

(22) Filed: Jan. 12, 2018

(65) Prior Publication Data

US 2018/0206810 A1     Jul. 26, 2018

(30) Foreign Application Priority Data

Jan. 23, 2017    (KR) .................. 10-2017-0010475

(51) Int. Cl.
    *G01T 1/17*            (2006.01)
    *A61B 6/00*            (2006.01)
    (Continued)

(52) U.S. Cl.
    CPC .......... *A61B 6/5247* (2013.01); *A61B 5/0077* (2013.01); *A61B 6/40* (2013.01);
    (Continued)

(58) Field of Classification Search
    CPC ........... A61B 6/58; A61B 6/5247; A61B 6/54; A61B 6/40; A61B 5/0077; G01T 1/17
    See application file for complete search history.

(56) References Cited

U.S. PATENT DOCUMENTS 5,323,443 A * 6/1994 Lary .................... G03B 42/047
                                                      378/162
5,623,528 A * 4/1997 Takeda ................. G01N 23/044
                                                         378/2
(Continued)

FOREIGN PATENT DOCUMENTS

| EP | 2727535 A1 | 5/2014 |
| JP | 2016209548 A | 12/2016 |
| WO | 2017111464 A1 | 6/2017 |

OTHER PUBLICATIONS

Extended European Search Report regarding Application No. 18151220.3, dated Jun. 15, 2018, 7 pages.

(Continued)

*Primary Examiner* — David P Porta
*Assistant Examiner* — Djura Malevic

(57) ABSTRACT

The present disclosure provides an X-ray imaging apparatus and control method thereof, by which the user's hand is photographed and information about a thickness of a subject, information about a photographed spot or information about a photographing angle may be easily obtained from the photographed image. According to an aspect of an example embodiment, there is an X-ray imaging apparatus comprising an X-ray source configured to generate and irradiate an X-ray; a photographing device equipped in the X-ray source for capturing a camera image; and a controller configured to detect a plurality of indicators from the camera image, calculate a thickness of an X-raying portion of a subject based on a distance between the plurality of indicators, and controlling an X-ray irradiation condition based on the thickness of the X-raying portion.

18 Claims, 15 Drawing Sheets

(51) Int. Cl.
  *A61B 5/00* (2006.01)
  *G01B 15/02* (2006.01)
  *A61B 6/08* (2006.01)
  *A61B 6/06* (2006.01)

(52) U.S. Cl.
  CPC .............. *A61B 6/54* (2013.01); *A61B 6/544* (2013.01); *G01B 15/02* (2013.01); *G01T 1/17* (2013.01); *A61B 6/06* (2013.01); *A61B 6/08* (2013.01); *A61B 6/4405* (2013.01); *A61B 6/4464* (2013.01)

(56) References Cited

U.S. PATENT DOCUMENTS

| | | | | |
|---|---|---|---|---|
| 6,447,163 | B1* | 9/2002 | Bani-Hashemi | A61B 6/08 378/205 |
| 7,885,439 | B2* | 2/2011 | Kato | A61B 5/489 382/128 |
| 8,203,132 | B2* | 6/2012 | Feke | A61B 5/0059 250/583 |
| 8,396,184 | B2* | 3/2013 | Shinno | A61B 6/469 378/5 |
| 9,855,018 | B2* | 1/2018 | Hamano | A61B 6/4233 |
| 9,974,504 | B2* | 5/2018 | Lee | A61B 6/469 |
| 10,285,664 | B2* | 5/2019 | Song | A61B 6/06 |
| 10,335,111 | B2* | 7/2019 | Enomoto | A61B 6/56 |
| 10,368,826 | B2* | 8/2019 | Tamura | H05G 1/44 |
| 10,660,599 | B2* | 5/2020 | Becker | A61B 6/547 |
| 2004/0125921 | A1* | 7/2004 | Allouche | A61B 6/544 378/207 |
| 2005/0169425 | A1* | 8/2005 | Takasawa | A61B 6/547 378/97 |
| 2006/0269004 | A1 | 11/2006 | Schmitt | |
| 2009/0122959 | A1* | 5/2009 | Jadrich | G01T 1/20 378/91 |
| 2011/0013752 | A1* | 1/2011 | Takahashi | A61B 6/583 378/205 |
| 2011/0110497 | A1* | 5/2011 | Nishino | A61B 6/542 378/98.8 |
| 2011/0129058 | A1* | 6/2011 | Ulrici | A61B 6/14 378/4 |
| 2011/0254922 | A1* | 10/2011 | Schaerer | A61B 90/96 348/46 |
| 2014/0355735 | A1* | 12/2014 | Choi | A61B 6/544 378/8 |
| 2015/0164440 | A1* | 6/2015 | Rackow | A61B 5/7485 600/427 |
| 2015/0272520 | A1* | 10/2015 | Kobayashi | A61B 6/487 378/62 |
| 2016/0154125 | A1* | 6/2016 | Kim | A61B 6/44 378/189 |
| 2016/0331334 | A1* | 11/2016 | Imamura | A61B 6/06 |
| 2017/0281108 | A1* | 10/2017 | Choi | A61B 6/582 |

OTHER PUBLICATIONS

Communication pursuant to Article 94(3) EPC dated Oct. 10, 2019 in connection with European Patent Application No. 18 151 220.3, 5 pages.

Communication pursuant to Article 94(3) EPC dated May 12, 2020 in connection with European Patent Application No. 18 151 220.3, 4 pages.

* cited by examiner

113: 113a, 113b, 113c, 113d

X-RAY IMAGING APPARATUS AND CONTROL METHOD THEREOF

CROSS-REFERENCE TO RELATED APPLICATION AND CLAIM OF PRIORITY

This application is related to and claims priority to Korean Patent Application No. 10-2017-0010475, filed on Jan. 23, 2017, the contents of which are incorporated herein by reference.

TECHNICAL FIELD

The present disclosure relates to an X-ray imaging apparatus equipped with a camera and control method thereof.

BACKGROUND

X-ray imaging apparatuses are devices for allowing the user to see an internal structure of a subject by irradiating X-rays to the subject and analyzing X-rays that have passed through the subject. X-ray transmittance is different depending on the tissue of a subject, so the internal structure of the subject may be imaged using an attenuation coefficient quantified from the X-ray transmittance.

Meanwhile, to set a condition for X-ray irradiation, information about a Source to Object Distance (SOD) representing a distance between an X-ray source and a subject and a Source to Image receptor Distance (SID) representing a distance between the X-ray source and an X-ray detector is required.

SUMMARY

To address the above-discussed deficiencies, it is a primary object to provide an X-ray imaging apparatus and control method thereof, by which the user's hand is photographed and information about a thickness of a subject, information about a photographed spot or information about a photographing angle may be easily obtained from the photographed image.

According to an aspect of an example embodiment, there is an X-ray imaging apparatus comprising an X-ray source configured to generate and irradiate an X-ray; a photographing device equipped in the X-ray source for capturing a camera image; and a controller configured to detect a plurality of indicators from the camera image, calculate a thickness of an X-raying portion of a subject based on a distance between the plurality of indicators, and controlling an X-ray irradiation condition based on the thickness of the X-raying portion.

The plurality of indicators may comprise both hands of a user.

The photographing device may comprise at least one of a three dimensional (3D) camera, a depth camera, and a stereo camera which are able to obtain depth information.

The camera image may have one of the hands of the user located in front of the X-raying portion of the subject and the other of the hands of the user located a distance of the thickness of the X-raying portion away from the one hand.

The X-ray irradiation condition may comprise at least one of a tube voltage, a tube current, an exposure time, a filter type, filter thickness, a target material of anode, a focal size, a grid angle, a center position of the grid, and a field of view (FOV).

The controller may be configured to calculate a distance between the hands using a camera image captured at a point when a preset event occurs if the preset event occurs.

The controller may be configured to determine that the preset event has occurred if recognizing that at least one of the hands makes a pre-registered gesture.

The controller may be configured to recognize an X-raying portion of the subject from the camera image and set an X-raying protocol based on the recognized X-raying portion.

The controller may be configured to recognize a portion where at least one of the hands of the user is located in the camera image as the X-raying portion.

The controller may be configured to control the X-ray irradiation condition based on the calculated distance between the hands and the set X-raying protocol.

The controller is configured to detect a center position of at least one of the hands of the user in the camera image and move the X-ray source to a position corresponding to the center position.

The controller is configured to detect an angle of at least one of the hands of the user in the camera image and control an angle of the X-ray source to correspond to the angle of the detected one hand.

The controller may be configured to detect the plurality of indicators in the camera image when performing X-raying in a portable mode.

According to an aspect of another example embodiment, there is a control method of an X-ray imaging apparatus, the method comprising: capturing a camera image using a photographing device equipped in an X-ray source; detecting a plurality of indicators in the camera image; calculating a thickness of an X-raying portion of a subject based on a distance between the plurality of indicators; and controlling an X-ray irradiation condition based on the thickness of the X-raying portion.

The plurality of indicators may comprise both hands of a user.

The photographing device may comprise a three dimensional (3D) camera able to acquire depth information.

The camera image may have one of the hands of the user located in front of the X-raying portion of the subject and the other of the hands of the user located a distance of the thickness of the X-raying portion away from the one hand.

The method may further comprise determining whether a preset event occurs, and the calculating a distance between the detected hands may comprise calculating a distance between the hands using a camera image captured at a point when the preset event occurs if the preset event occurs.

Determining whether a preset event occurs may comprise determining that the preset event has occurred if recognizing that at least one of the hands makes a pre-registered gesture.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
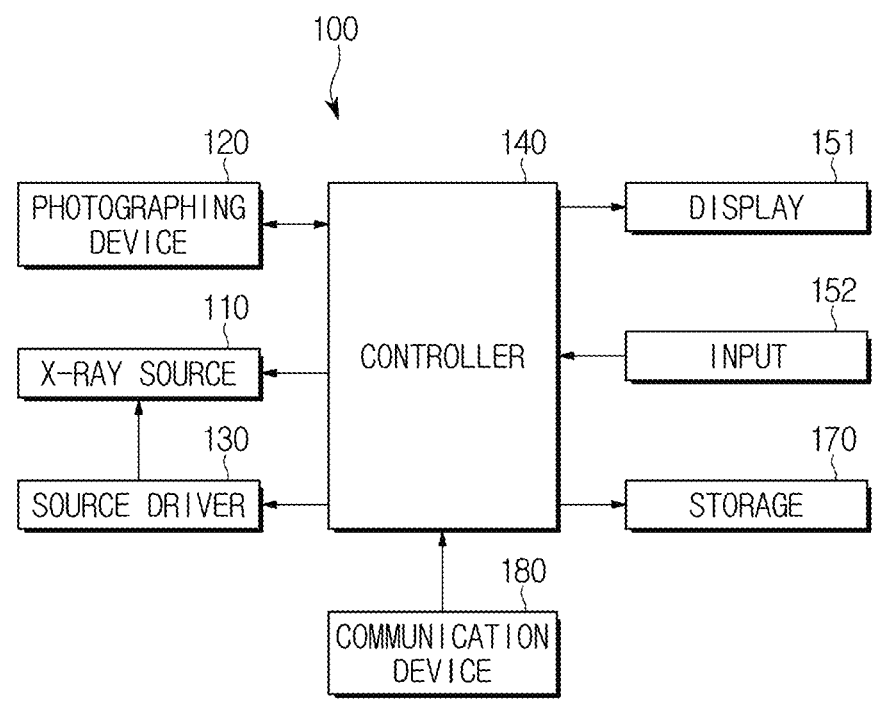
FIG. 1 illustrates a control block diagram of an X-ray imaging apparatus, according to an embodiment of the present disclosure.

FIGS. 1 through 14, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Like numerals refer to like elements throughout the specification. Not all elements of embodiments of the present disclosure will be described, and description of what are commonly known in the art or what overlap each other in the embodiments will be omitted. The terms as used throughout the specification, such as "~ part", "~ module", "~ member", "~ block", etc., may be implemented in software and/or hardware, and a plurality of "~ parts", "~ modules", "~ members", or "~ blocks" may be implemented in a single element, or a single "~ part", "~ module", "~ member", or "~ block" may include a plurality of elements.

It will be further understood that the term "connect" or its derivatives refer both to direct and indirect connection, and the indirect connection includes a connection over a wireless communication network.

The term "include (or including)" or "comprise (or comprising)" is inclusive or open-ended and does not exclude additional, unrecited elements or method steps, unless otherwise mentioned.

Throughout the specification, when it is said that a member is located "in front of" or "in the back of" another member, it implies not only that the member is located adjacent to the other member but also that a third member exists between the two members.

It is to be understood that the singular forms "a," "an," and "the" include plural references unless the context clearly dictates otherwise.

Reference numerals used for method steps are just used to identify the respective steps, but not to limit an order of the steps. Thus, unless the context clearly dictates otherwise, the written order may be practiced otherwise.

Embodiments of an X-ray imaging apparatus and control method thereof will now be described in detail with reference to accompanying drawings.

Figure 2:
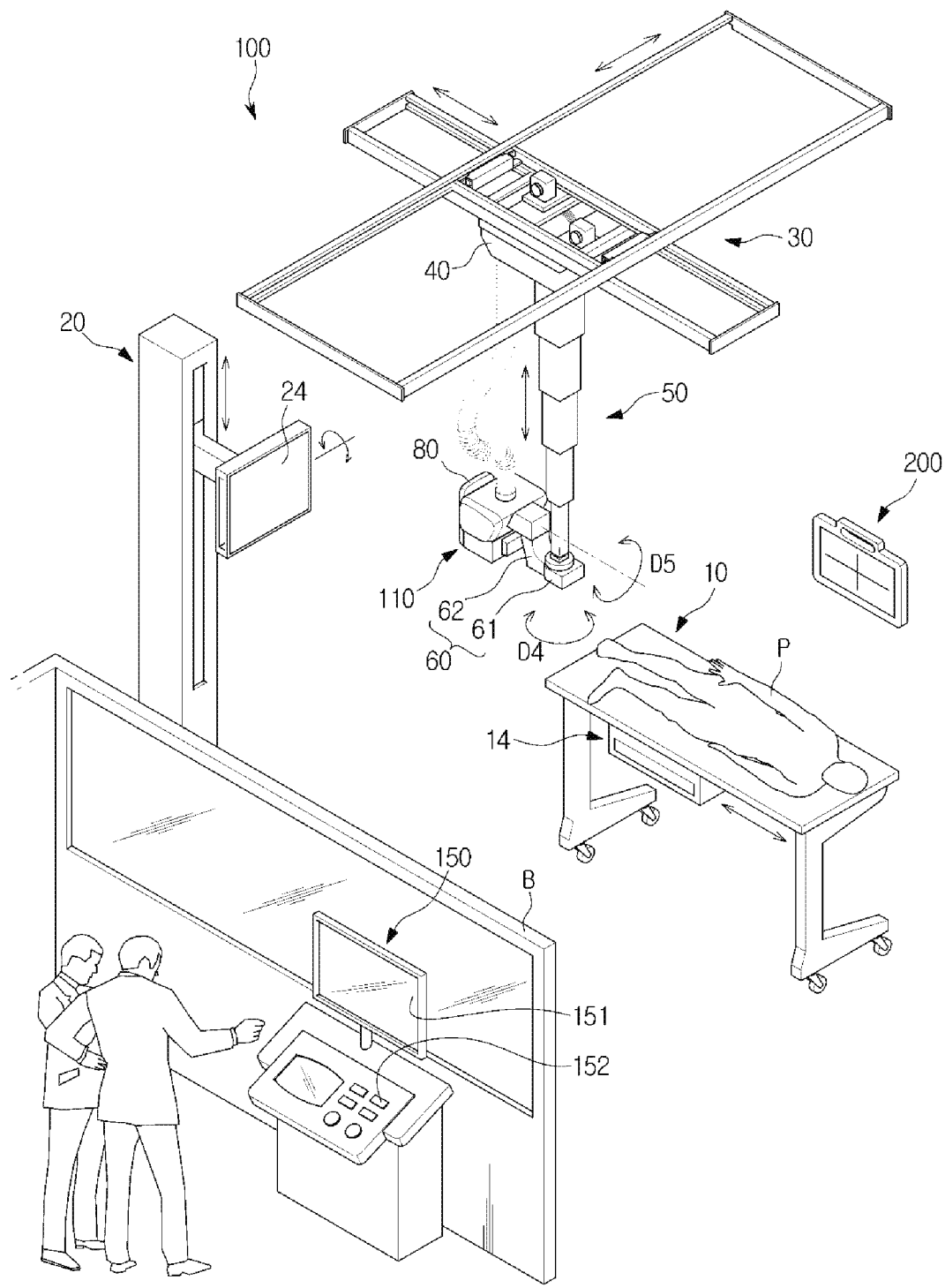
FIG. 2 is an exterior view illustrating a configuration in which an X-ray imaging apparatus is implemented in a ceiling type, according to an embodiment of the present disclosure.
Figure 3:
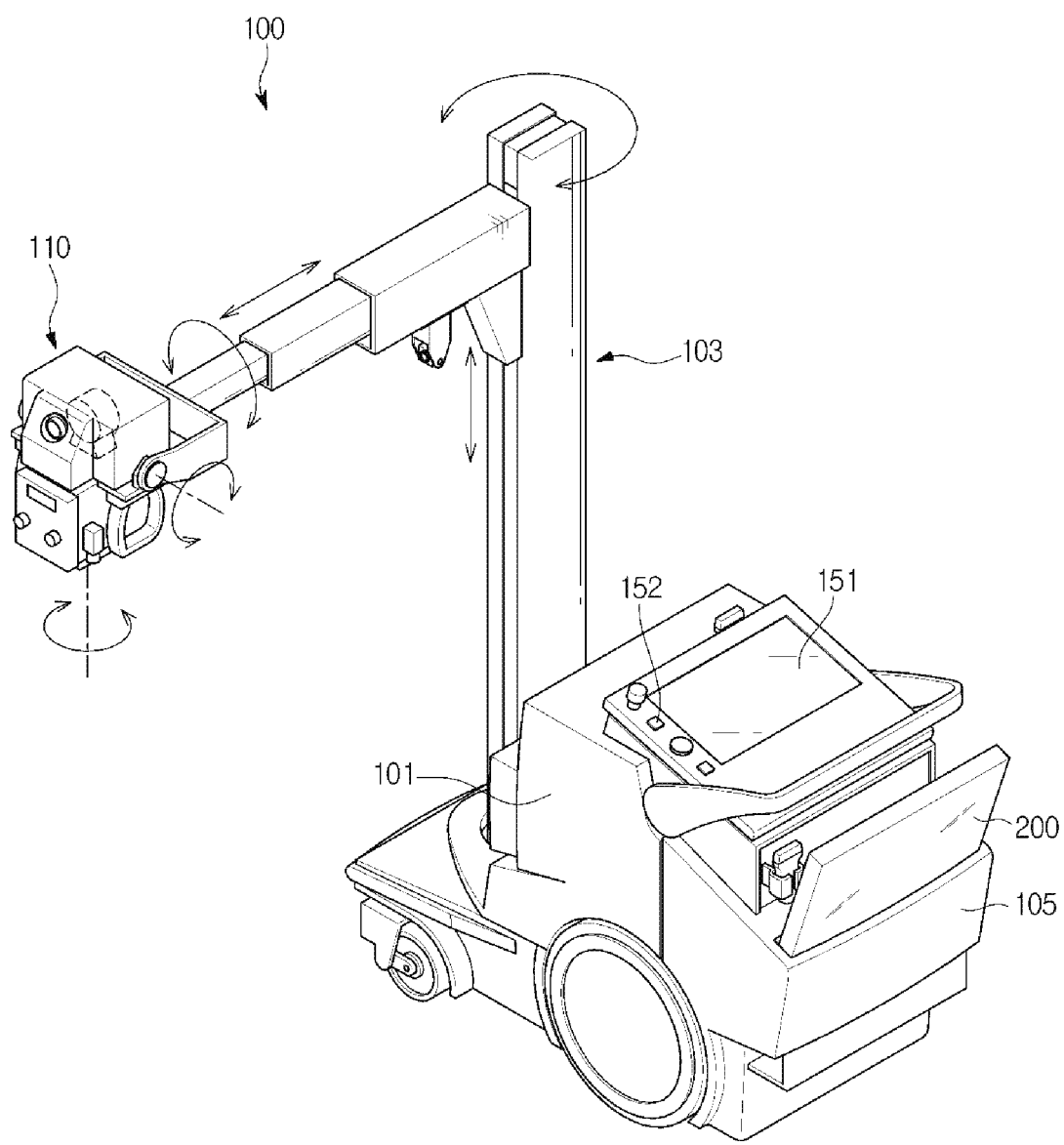
FIG. 3 is an exterior view illustrating a configuration in which an X-ray imaging apparatus is implemented in a mobile type according to an embodiment of the present disclosure.

FIG. 1 illustrates a control block diagram of an X-ray imaging apparatus, according to an embodiment of the present disclosure, FIG. 2 is an exterior view illustrating a configuration in which an X-ray imaging apparatus is implemented in a ceiling type, according to an embodiment of the present disclosure, FIG. 3 is an exterior view illustrating a configuration in which an X-ray imaging apparatus is implemented in a mobile type according to an embodiment of the present disclosure.

Referring to FIG. 1, an X-ray imaging apparatus 100 in accordance with an embodiment may include an X-ray source 110 for generating and irradiating an X-ray to a subject, a photographing device 120 equipped in the X-ray source 110 for capturing a camera image, a source driver 130 for moving the X-ray source 110, a controller 140 for analyzing the camera image captured by the photographing device 120 to determine thickness of the subject and controlling a condition for X-ray radiation based on the thickness of the subject, a display 151 for displaying a screen to provide information about X-raying for the user, a screen to guide a control command input by the user, a camera image or X-ray image captured by the photographing device 120, etc., an input 152 for receiving a control command from the user, a storage 170 for storing X-ray irradiation conditions per thickness of a subject, and a communication device 180 for exchanging data in communication with an X-ray detector 200 or other external devices.

Operations of the respective components of the X-ray imaging apparatus 100 will now be described in detail with reference to accompanying drawings.

FIG. 2 illustrates an example of an X-ray imaging apparatus, which is a ceiling type X-ray imaging apparatus with an X-ray source attached to the ceiling of an examination room.

Referring to FIG. 1, a guide rail 30 may be installed on the ceiling of the examination room where the X-ray imaging apparatus 100 is placed, and the X-ray source 110 linked to a moving carriage 40 that moves along the guide rail 30 may be moved to a position corresponding to the subject.

The moving carriage 40 and the X-ray source 110 may be linked through a foldable post frame 50, and the altitude of the X-ray source 110 may be adjusted by shortening or extending the length of the post frame 50.

A rotary joint 60 is arranged between the X-ray source 110 and the post frame 50. The rotary joint 60 may include a first rotary joint 61 coupled to the post frame 50 and a second rotary joint 62 coupled to the X-ray source 110.

The first rotary joint 61 may be rotated in a fourth direction D4 and the second rotary joint 62 may be rotated in a fifth direction D5. By rotating the second rotary joint 62 in the fifth direction D5, a tilt angle of the X-ray source 110 may be adjusted. The posture of the X-ray source 110 may be defined by a rotation angle in the fourth direction D4 or a tilt angle in the fifth angle D5.

The source driver 130 may include a plurality of motors to provide power required to move the X-ray source 110 straight or rotate the X-ray source 110. The controller 140 may adjust the position or posture of the X-ray source 110 by controlling the source driver 130.

The X-ray source 110 may be equipped with an X-ray tube for generating an X-ray and a collimator for adjusting an irradiation area of an X-ray generated by the X-ray tube. Accordingly, the X-ray source 110 may also be called a Tube Head Unit (THU).

The photographing device 120 for capturing a camera image may also be equipped in the X-ray source 110. Where to install the photographing device 120 will be described later.

The X-ray imaging apparatus 100 may include a workstation 150 located a distance away from the X-ray source 110 for providing a user interface. The X-ray source 110 and the workstation 150 may have a blackout curtain B arranged in between to prevent a radiological technologist, a doctor, or the user from being unnecessarily exposed to radiation.

The workstation 150 may be equipped with the input 152 for receiving a control command from the user and a display 151 for displaying various kinds of information and images.

The input 152 may receive commands to control an X-raying protocol, an X-ray irradiation condition, an X-ray irradiation timing, a position or posture of the X-ray source 110, etc., or command for capturing camera images. The input 152 may include a keyboard, a mouse, a touch screen, a microphone, etc.

The display 151 may display a screen to guide the user in selecting an X-raying protocol, a screen to guide the user in setting an X-ray irradiation condition, a screen to receive a control command for X-ray irradiation timing or positioning of the X-ray source 110, etc. Furthermore, the display 151 may display a screen to show a current state of workflows for X-raying, or display a camera image captured by the photographing device 120, or display an X-ray image of the subject.

The controller 140 may control X-ray irradiation timing, X-ray irradiation conditions, etc., according to a command entered by the user, and create a medical X-ray image using data received from the X-ray detector 200.

The controller 140 may also control a position or posture of an install portion 14, 24 in which the X-ray source 110 or the X-ray detector 200 is installed, according to the X-raying protocol and a position of a subject P.

The controller 140 may include a memory storing a program for carrying out the aforementioned operations and the following operations, and a processor for executing the program, and may be equipped in the workstation 150.

The controller 140 may include a single processor or multiple processors, and in the latter case, the multiple processors may be integrated in a single chip or may be physically separated.

In the case that the controller 140 includes the multiple processors, some of the multiple processors may be included in the workstation 150, and some others in a sub-user interface 80 equipped in the X-ray source 110, the moving carriage 40, or other device. For example, the processor(s) included in the workstation 150 may perform control, such as image processing to create an X-ray image, and the processor(s) included in the sub-user interface 80 or the moving carriage 40 may perform control over the operation or movement of the X-ray source 110 or the X-ray detector 200.

The X-ray imaging apparatus 100 may be connected to the X-ray detector 200 or an external device (e.g., an external server for storing and managing medical images, another medical device and a portable terminal such as a tablet Personal Computer (PC) and a wearable device) for exchanging data through the communication device 180.

The communication device 180 may include one or more components that enable communication with an external device, for example, at least one of a short-range communication module, a wired communication module, and a wireless communication module.

The communication device 180 may also receive a control signal from the external device and forward the control signal for the controller 140 to control the X-ray imaging apparatus 100 according to the control signal.

The X-ray detector 200 may be implemented as a fixed type of X-ray detector fixed on a stand 20 or a table 10, or may detachably equipped in the install portion 14, 24. Alternatively, the X-ray detector 300 may be implemented as a portable X-ray detector available at any place. The portable X-ray detector may further be classified into a wired type and a wireless type depending on the data transfer method or the power supplying method.

The X-ray detector 200 may or may not be included as an element of the X-ray imaging apparatus 100. In the latter case, the X-ray detector 200 may be registered in the X-ray imaging apparatus 100 by the user.

The X-ray detector 200 may be connected to the controller 140 through the communication device 180 for receiving a control signal or sending image data.

The sub-user interface 80 may be arranged on one side of the X-ray source 110, and may perform a part or all of the functions performed by the input 152 and the display 151 of the workstation 150.

If all or part of the components of the controller 140 and the communication device 180 are provided separately from the workstation 150, they may be included in the sub-user interface 80 arranged on the X-ray source 110.

The X-ray imaging apparatus 100 may be implemented not only in the ceiling type but also in a mobile type. In the case that the X-ray imaging apparatus 100 is implemented in the mobile type, as shown in FIG. 3, a main body 101 connected to the X-ray source 110 may be freely movable and an arm 103 connecting the X-ray source 110 and the main body 101 is also be able to rotate and make linear motions, enabling the X-ray source 110 to be freely moved in the three dimensional (3D) space.

The main body 101 may have a keeper 105 for keeping the X-ray detector 200. Furthermore, the keeper 105 may also have a charging terminal provided therein to charge the X-ray detector 200, so it is possible for the keeper 105 to be able to keep and charge the X-ray detector 200.

The input 152, the display 151, the controller 140, and the communication device 180 may be provided in the main body 101, and image data acquired by the X-ray detector 200 may be sent to the main body 101 to go through image processing and then displayed on the display 151 or sent to the external device through the communication device 180.

The controller 140 and the communication device 180 may be provided separately from the main body 101, or some of the components of the controller 140 and the communication device 180 may be provided in the main body 101.

Figure 4:
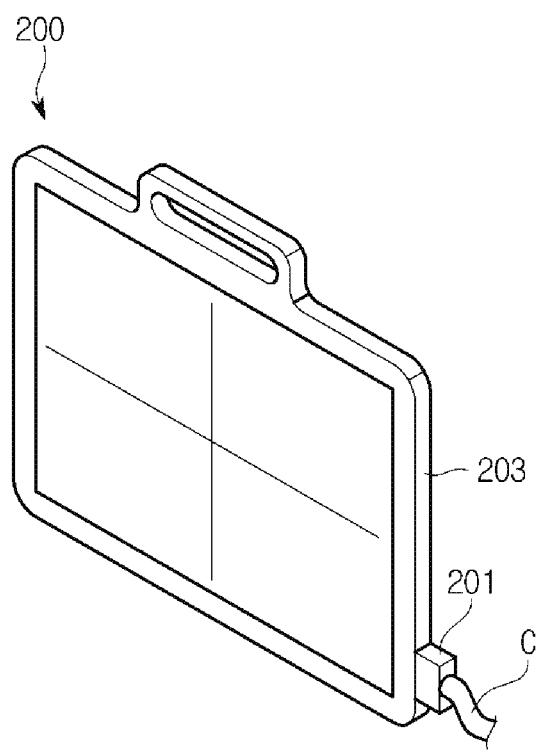
FIG. 4 illustrates an exterior view of a portable X-ray detector available for an X-ray imaging apparatus according to an embodiment of the present disclosure.

FIG. 4 illustrates an exterior view of a portable X-ray detector available for an X-ray imaging apparatus according to an embodiment of the present disclosure;

As described above, the X-ray detector 200 available for the X-ray imaging apparatus 100 may be implemented in a portable type. In this case, the X-ray detector 200 may include a battery to supply power and thus, operate wirelessly, or as shown in FIG. 4, may have a charging port 201 connected to a separate power supplier via a cable C.

Inside a case 203 of the X-ray detector 200 forming the exterior, there may be a detecting device for detecting and converting an X-ray to image data, a memory for temporarily or non-temporarily storing the image data, a communication module for receiving a control signal from the X-ray imaging apparatus 100 or transmitting image data to the X-ray imaging apparatus 100, and a battery.

The memory may store image correction information of the detector and unique identification information of the X-ray detector 200, and may send the identification information while communicating with the X-ray imaging apparatus 100.

The X-ray detector 200 may be installed in the install portion 14 of the imaging table 10 or in the installation portion 24 of the imaging stand 20, but it is also possible to perform X-ray imaging without installing the X-ray detector 200 in the install portion 14, 24 depending on a condition or a portion to be photographed of the subject. In this case, X-raying may be performed by irradiating an X-ray to a portion to be photographed (or called an imaging portion) while the X-ray detector 200 is located behind the imaging portion.

In the embodiment, a mode in which X-raying is performed with the X-ray detector 200 installed in the install portion 14 of the imaging table 10 is called a table mode; a mode in which X-raying is performed with the X-ray detector 200 installed in the install portion 24 of the imaging stand 20 is called a stand mode; a mode in which X-raying is performed with the X-ray detector 200 not installed in the install portion 14, 24 but located behind an imaging portion of the subject is called a portable mode.

An X-ray irradiation condition may be determined depending on the feature of the subject or the imaging environment. The X-ray irradiation condition may include at least one of exposure parameters, such as a tube voltage (Kvp), a tube current (mA), exposure time (s), a filter type and thickness, a target material of anode, focal spot size, etc., and scatter parameters, such as a grid angle or center position, field of view (FOV), etc.

Especially, in determining the X-ray irradiation condition, the thickness of the subject may be considered. For example, the controller 140 may obtain the thickness of the subject in a way of subtracting the Source to Object Distance (SOD) from the Source to Image Distance (SID). In this case, to obtain the thickness of the subject, information about the SID and SOD is required.

Furthermore, in a case of an automatic moving mode to automatically perform alignment of position and posture of the X-ray source 110, to align the position and posture of the X-ray source 110, information about the portion to be X-rayed or the position and posture of the X-ray detector 200 is required.

In an embodiment, the X-ray imaging apparatus 100 may obtain information about thickness of the subject and information about the portion to be X-rayed or the position and posture of the X-ray detector 200 from a camera image captured by the photographing device 120.

Figure 5:
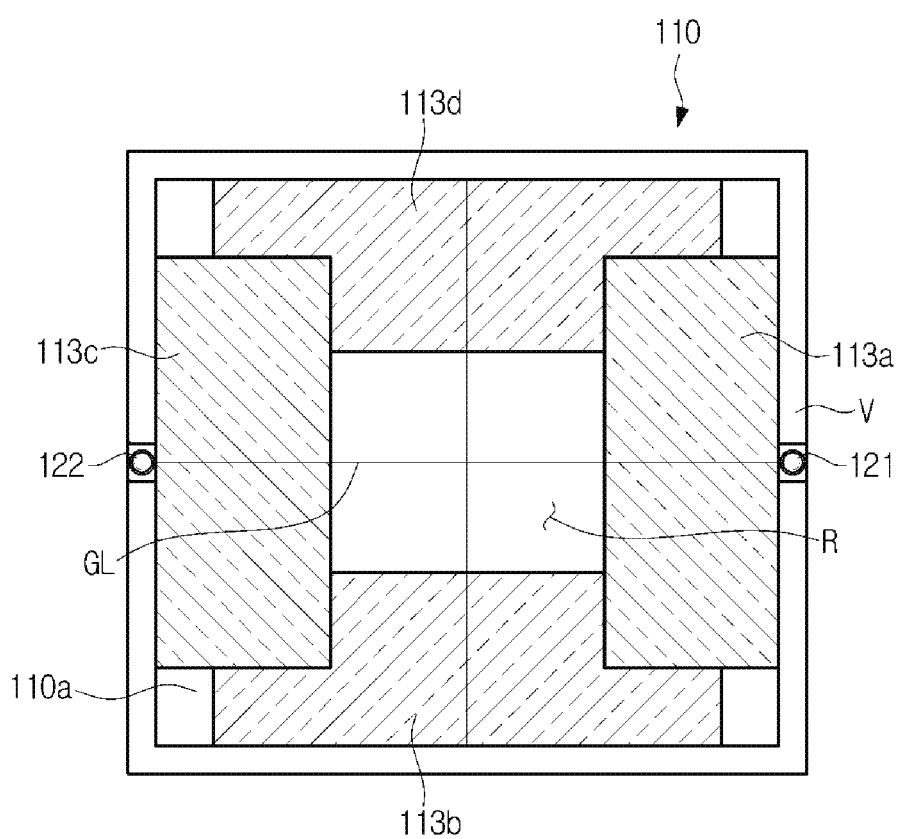
FIG. 5 illustrates a front view of an X-ray source of an X-ray imaging apparatus, according to an embodiment of the present disclosure.

FIG. 5 illustrates a front view of an X-ray source of an X-ray imaging apparatus, according to an embodiment of the present disclosure. The front view as herein used refers to a view of the X-ray source viewed from a direction in which an X-ray is irradiated.

As described above, the X-ray source 110 may include the X-ray tube for generating an X-ray and the collimator 113 for adjusting an irradiation range of the X-ray. The collimator 113 is located in front of the X-ray tube, i.e., in a direction in which the X-ray is irradiated.

Referring to FIG. 5, the collimator 113 may include a plurality of movable blades 113a, 113b, 113c, 113d, and the blades may be made of a material with high bandgap to absorb the X-ray. The X-ray irradiation range may be adjusted by moving the blades, and the X-ray is irradiated through a slot R formed by the plurality of blades.

The collimator 113 may further include a motor for providing driving force to the respective blades. Each of the plurality of blades may be independently moved. The controller 140 may calculate an amount of movement of each blade to irradiate an X-ray to a set irradiation region, and send a control signal to the collimator 113 to move the blade as much as the calculated amount of movement.

The photographing device 120 may be provided in an area adjacent to the collimator 113.

While the X-ray source 110 and the X-ray detector 200 take an X-ray image, the photographing device 120 may take a real image. The real image taken by the photographing device 120 may be a moving image or a still image. While a moving image is being taken, a still image may be captured at a particular point of time. In the embodiment, the image taken by the X-ray source 110 is classified as an X-ray image, and the image taken by the photographing device 120 is classified as a camera image.

The camera image may or may not include the subject. For example, the camera image may be taken when the subject P is located in front of the X-ray detector 200, or may be taken when the subject P is not present.

The camera image may or may not include the user. The user as herein used may be an entity that performs X-raying on the subject by operating the X-ray apparatus 100, such as a radiological technologist, a doctor, a nurse, etc.

The photographing device 120 may be placed in a position where a portion to be X-rayed of the subject may be photographed. For example, it may be installed to be directed toward the same direction in which the X-ray source 110 irradiates an X-ray. Once the photographing device 120 is installed in the X-ray source 110, an offset between an area appearing in the X-ray image and an area appearing in the camera image becomes small, so it may be easier to perform X-ray image related setting by using the camera image. The position to install the photographing device 120 may be determined within a range that may give little influence to X-raying while minimize the offset between the area appearing in the X-ray image and the area appearing in the camera image.

A housing 110a is formed in front of the collimator 113 and may be made of a material such as a transparent resin or glass to minimize its influence to an X-ray irradiated from the X-ray tube 111.

Furthermore, cross guide lines GL may be marked on the housing 110a. When a collimator lamp equipped in the X-ray source 110 irradiates a visible ray into an X-ray irradiation area, the shadow of the guide line GL may be projected down on the center of the X-ray irradiation area, enabling the user to intuitively know of the position of the X-ray irradiation area from the shadow.

The photographing device 120 may be installed inside or outside the housing 110a. If the photographing device 120 is installed outside the housing 110a, it may be mounted in a bezel V formed on the perimeter of the housing 110a. It is, however, not limited thereto, and the photographing device 120 may be installed at any place that allows taking an image including the subject or the user.

The photographing device 120 may include a 3D camera for acquiring 3D information. For example, the photographing device 120 may include a stereo camera or a depth camera to acquire depth information of the object present in a scene.

In the case that the photographing device 120 includes the stereo camera, as shown in FIG. 5, cameras 121, 122 may be equipped on the front left and right sides of the X-ray source 110. The controller 140 may perform stereo matching with camera images captured by the left and right cameras 122, 121, and thus calculate the depth information of the object, which appears in the camera images.

However, the cameras 121, 122 shown in FIG. 5 are only an example available for the X-ray imaging apparatus 100, and it is also possible to have three or more cameras to obtain multi-view images for more accurate calculation of depth information.

In a case that the photographing device 120 is implemented with a depth camera, it may include an infrared sensor and a color camera to acquire the depth information of an object. For example, two color cameras may be installed on the front left and right sides of the X-ray source 110, and an infrared sensor may be installed between the two cameras.

The depth camera may acquire the depth information using a Time-of-Flight (TOF) technology. The TOF technology is to measure a distance by calculating time for an infrared signal to reflect off a subject and return.

The controller 140 may obtain thickness information of the subject (P) from a camera image including depth information of the subject. Specifically, the controller 140 may detect a plurality of indicators from the camera image. One of the plurality of indicators may be located on the front face of an X-raying portion of the subject P, and the other may be located at a distance of the thickness of the X-raying portion away from the front face. The front face herein refers to a surface on which the X-ray is incident. Accordingly, the controller 140 may calculate the thickness of the subject P based on the distance between the plurality of indicators.

For example, the plurality of indicators may include both hands of the user. The user may put one hand on the front face of the X-raying portion of the subject while putting the other hand at a distance of the thickness of the X-raying portion away from the front face. An example of using both hands of the user as the plurality of indicators will now be described in detail.

Figure 6:
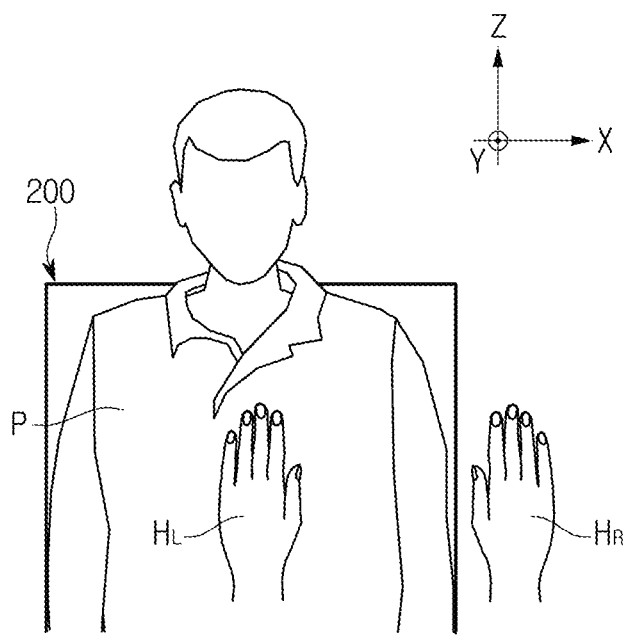
FIG. 6 illustrates positions of the user's hands viewed from the front of a portion to be X-rayed to obtain thickness information of a subject.
Figure 7:
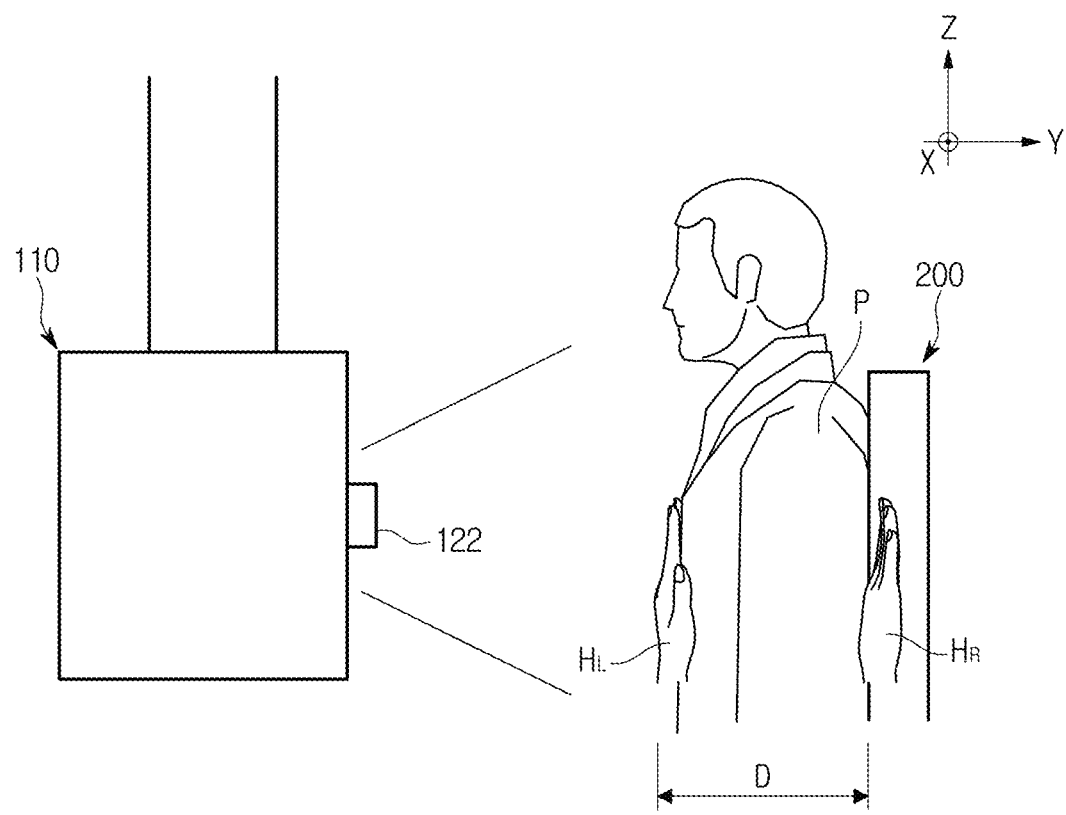
FIG. 7 illustrates positions of the user's hands viewed from a side of a portion to be X-rayed to obtain thickness information of a subject.

FIG. 6 illustrates positions of the user's hands viewed from the front of a portion to be X-rayed to obtain thickness information of a subject, and FIG. 7 illustrates positions of the user's hands viewed from a side of the portion to be X-rayed to obtain thickness information of the subject.

In FIGS. 6 and 7, it is assumed that the X-ray detector 200 is located in the back of the portion to be X-rayed (or called the X-raying portion) of the subject P in the portable mode to perform X-raying.

Referring to FIGS. 6 and 7, the user places one hand $H_L$ in front of the X-raying portion of the subject P while placing the other hand $H_R$ at the same point as the X-ray detector 200 on the Y-axis. For example, the distance between the hand $H_L$ placed in front of the X-raying portion and the X-ray detector 200 is equal to the distance between the hand $H_L$ and the other hand $H_R$. Accordingly, the distance on the Y-axis between the hands $H_L$, $H_R$ of the user may be assumed to be equal to or almost similar to the thickness D of the X-raying portion of the subject P.

In the portable mode, it is difficult to know of the SID or thickness of the subject because the position of the X-ray detector is not fixed, but in the embodiment, the thickness of the subject may be measured without extra equipment or tools by using the hands of the user appearing in a camera image.

In this regard, to ensure that the hands $H_L$, $H_R$ of the user are taken by the photographing device 120, they should not be hidden by the subject P or the X-ray detector 200.

Although it is assumed that the X-ray detector 200 is located in the back of the X-raying portion in the embodiment of FIGS. 6 and 7, it is possible to capture a camera image to acquire the thickness information of the X-raying portion before placing the X-ray detector 200. Even in this case, one hand $H_L$ of the user may be placed in front of the X-raying portion of the subject P and the other hand $H_R$ may be placed at the same point as the X-ray detector 200 on the Y-axis.

The photographing device 120 may have been taking camera images before the hands $H_L$, $H_R$ of the user are placed a distance of the thickness D of the subject away from each other. For example, the user may manipulate the input 152 from when beginning preparing for X-ray imaging and enter a command to capture a camera image, and the photographing device 120 may start taking a moving image according to the command.

If a preset event occurs during the capturing of a camera image, the thickness D information of the subject may be obtained by calculating a distance between the hands of the user from a camera image captured at the point when the event occurs. This will now be described with reference to FIG. 8.

Figure 8:
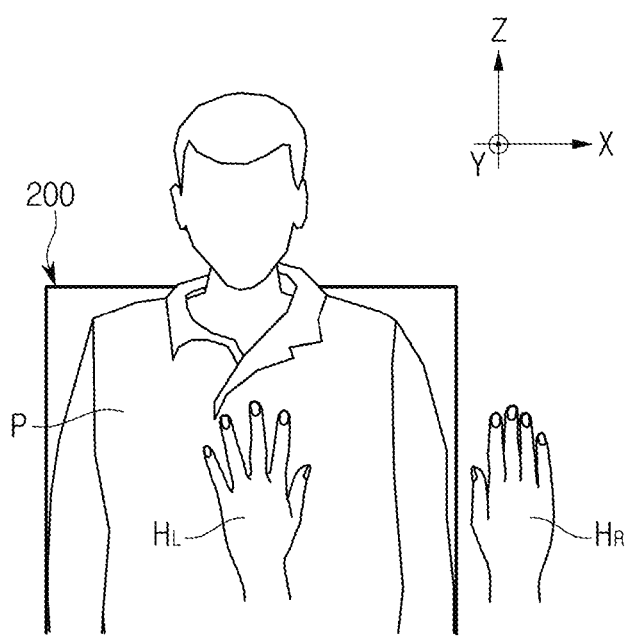
FIG. 8 illustrates an example of a gesture functioning as a specific event to obtain thickness information of a subject.

FIG. 8 illustrates an example of a gesture functioning as a specific event to obtain thickness information of a subject.

Referring to FIG. 8, if the user makes a pre-registered gesture with one hand $H_L$ after placing the hands $H_L$, $H_R$ a distance of the thickness D of the subject away from each other, the controller 140 may determine that a preset event has occurred and calculate the thickness D of the subject using the positions of the hands $H_L$, $H_R$ at the point when the event has occurred.

Although the gesture of the user spreading one hand $H_L$ is registered in advance in the example of FIG. 8, embodiments of the present disclosure are not limited thereto but any gesture that may be recognized by an image recognition algorithm may be an event to indicate time to measure the thickness of the subject.

For example, the controller 140 may recognize the user's hand appearing in the camera image by means of an object recognition algorithm and recognize a gesture made by the user's hand using a gesture recognition algorithm. If the recognized gesture corresponds to a pre-registered gesture, it is considered that the event to measure the thickness D of the subject has occurred, and subsequently, the thickness D of the subject may be calculated using the camera image captured at the time the event has occurred. Since every portion of the subject may have different thickness, to be precise, the thickness of the X-raying portion may be calculated.

For example, the controller 140 may control the photographing device 120 to capture a still image at the point when the event occurs, and calculate the thickness D of the X-raying portion using the captured still image.

As described above, the photographing device 120 may include a 3D camera that may acquire depth information of an object appearing in a camera image, so the controller 140 may obtain depth information of each of the hands $H_L$, $H_R$ appearing in the camera image. The depth information as herein used may refer to a distance between the photographing device 120 and either hand $H_L$, $H_R$.

Specifically, the controller 140 may use an object recognition algorithm to recognize each of the hands $H_L$, $H_R$ appearing in the camera image and calculate the depth of either hand $H_L$, $H_R$. The depth of the hand $H_L$ placed in front of the X-raying portion may be estimated to correspond to the SOD, and the depth of the hand $H_R$ placed in the back of the X-raying portion may be estimated to correspond to the SID.

The controller 140 may obtain the thickness D of the X-raying portion from the difference in thickness between the hand $H_L$ placed in front of the X-raying portion and the hand $H_R$ placed in the back of the X-raying portion. That is, the distance between the hands $H_L$, $H_R$ appearing in the camera image may be estimated to be the thickness D of the X-raying portion.

As described above, the X-ray irradiation condition may vary by the thickness D of the X-raying portion. Accordingly, the controller 140 may control the X-ray irradiation condition based on the thickness information obtained from the camera image and the X-ray irradiation conditions by thickness of the X-raying portion may be stored in the storage 170 in advance.

The X-ray irradiation condition may vary by X-raying protocol as well. Specifically, the X-raying portion may vary by imaging protocol, and a suitable X-ray irradiation condition may vary by X-raying portion.

The X-raying protocol may be determined based on the X-raying portion, the posture of the object, etc., and may include, for example, the whole body Anterior-Posterior (AP), the whole body Posterior-Anterior (PA), the whole body LAT. Even for the chest, there may be imaging protocols for capturing images in the AP, PA, LAT methods, and for long bones such as legs, there may be imaging protocols for capturing images in the AP, PA, LAT methods. Furthermore, Abdomen Erect may also be included in the imaging protocol.

The controller 140 may recognize an X-raying portion and posture from a camera image by applying an object recognition algorithm, and may automatically set an X-raying protocol based on the result of recognition. In this regard, the controller 140 may recognize a portion where there are the user's hands $H_L$, $H_R$ as an X-raying portion.

The controller 140 may also automatically set an X-ray irradiation condition based on the thickness of the X-raying portion and the X-raying protocol. Information about the X-ray irradiation condition based on the thickness of the X-raying portion and the X-raying protocol may be stored in the storage 170 in advance.

Figure 9:
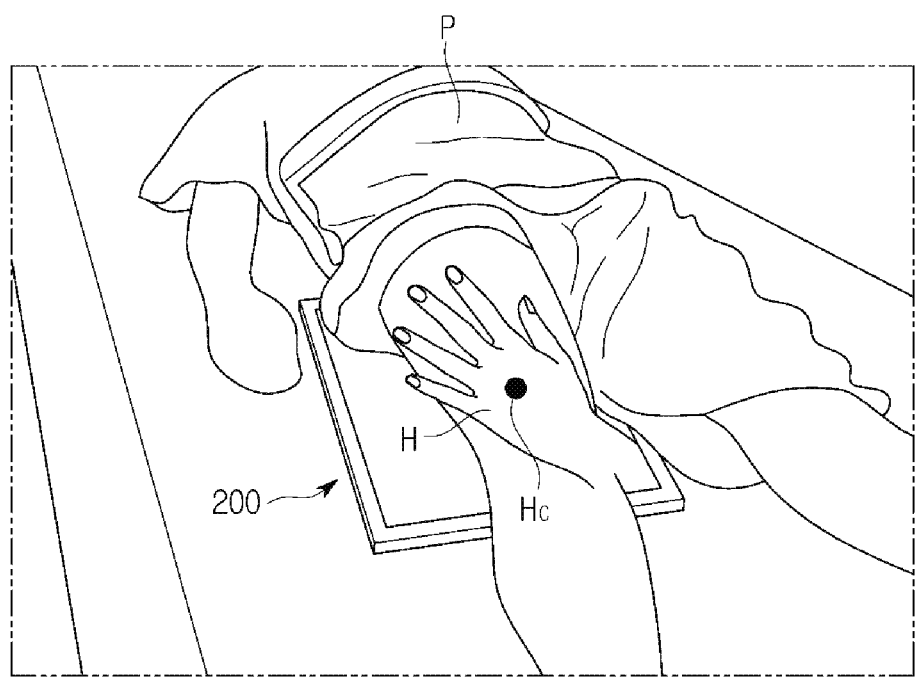
FIG. 9 illustrates how to control a position of an X-ray source using a position of the user's hand, according to an embodiment of the present disclosure.
Figure 10A:
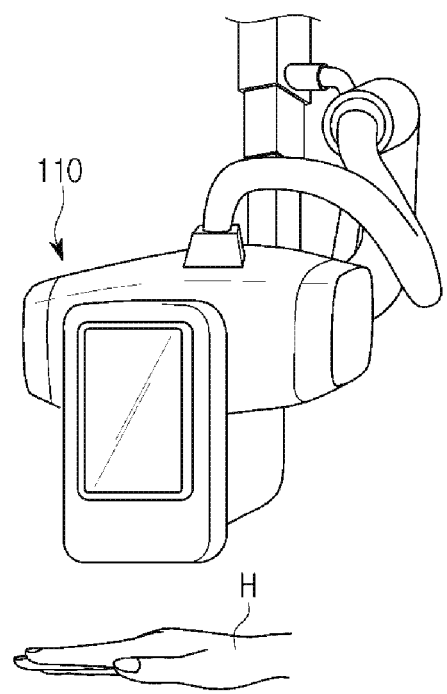
FIGS. 10A and 10B illustrate an example of controlling an angle of an X-ray source using an angle of the user's hand, according to an embodiment of the present disclosure.
Figure 10B:
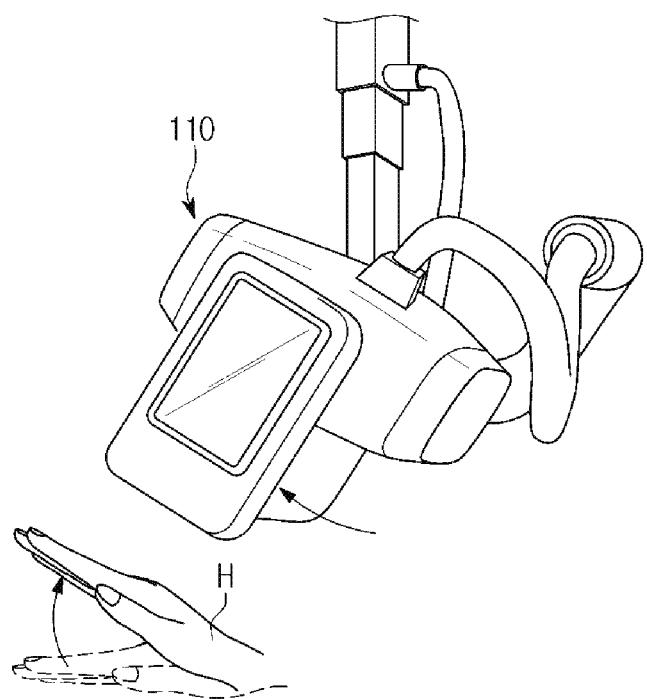

FIG. 9 illustrates how to control a position of an X-ray source using the position of the user's hand, according to an embodiment of the present disclosure, and FIGS. 10A and 10B illustrate an example of controlling an angle of an X-ray source using an angle of the user's hand, according to an embodiment of the present disclosure.

As described above, it is also possible to automatically control the position and posture of the X-ray source 110. In controlling the position and posture of the X-ray source 110, a camera image captured by the photographing device 120 may be used.

As shown in FIG. 9, the controller 140 may control the position of the X-ray source 110 by using a camera image in which a hand H of the user placed in the X-raying portion appears. For example, the camera image used for measuring the thickness D of the X-raying portion may be used. However, the sequence of measuring the thickness and controlling the position of the X-ray source 110 is not fixed. For example, conveniently, the thickness may be measured first or the position of the X-ray source 110 may be controlled first.

The controller 140 may recognize the hand H of the user from the camera image and detect the position of the recognized hand H. For more precise position control, a center Hc of the hand H may be recognized and the position of the hand's center Hc may be detected. Since the photographing device 120 includes a 3D camera, the position of the hand's center Hc may be calculated in 3D coordinates in a camera coordinate system.

The controller 140 may calculate an amount of control to correspond the position of the X-ray tube to the position of the hand's center Hc based on the relationship between the camera coordinate system and a global coordinate system in real space and a relative position of the X-ray tube and the photographing device 120.

The controller 140 may send a control signal corresponding to the calculated amount of control to the source driver 130 to control the position of the X-ray source 110 by moving or rotating the moving carriage 40, the post frame 50, or the rotary joint 60.

Furthermore, in some cases, it is necessary to control the posture of the X-ray source 110 depending on the posture of the subject P or the X-raying portion. In this case, as shown in FIGS. 10A and 10B, the user may rotate the angle of the hand H to correspond to the angle of the X-raying portion, and the controller 140 may detect a rotation angle of the hand H from the camera image and use the rotation angle to control the posture of the X-ray source 110.

For example, in a case that the camera image used for measurement of thickness is also used in controlling the posture of the X-ray source 110, the angle of the hand placed in front or back of the X-raying portion may correspond to the angle of the X-raying portion. The angle as herein used refers to an angle from the ground.

The controller 140 may detect an angle of the hand H from a camera image including 3D information, and calculate an amount of control to correspond the posture of the X-ray source 110 to the detected angle.

The controller 140 may control a rotation angle of the X-ray source 110 in the fourth direction D4 or in the fifth D5 direction by sending a control signal corresponding to the calculated amount of control to the source driver 130 and rotating the rotary joint 60.

In an embodiment, the X-ray imaging apparatus 110 may not be restricted to the sequence of calculation of the thickness of the X-raying portion and control of the position and posture of the X-ray source 110, but no matter which operation is performed first, the X-ray source 110 should be located at a point to capture a camera image of the X-raying portion.

An embodiment of a control method of an X-ray imaging apparatus will now be described. In the control method of an X-ray imaging apparatus, the X-ray imaging apparatus 100 may be used. Accordingly, what are described in connection with FIGS. 1 to 10 may be equally applied to the control method of the X-ray imaging apparatus.

Figure 11:
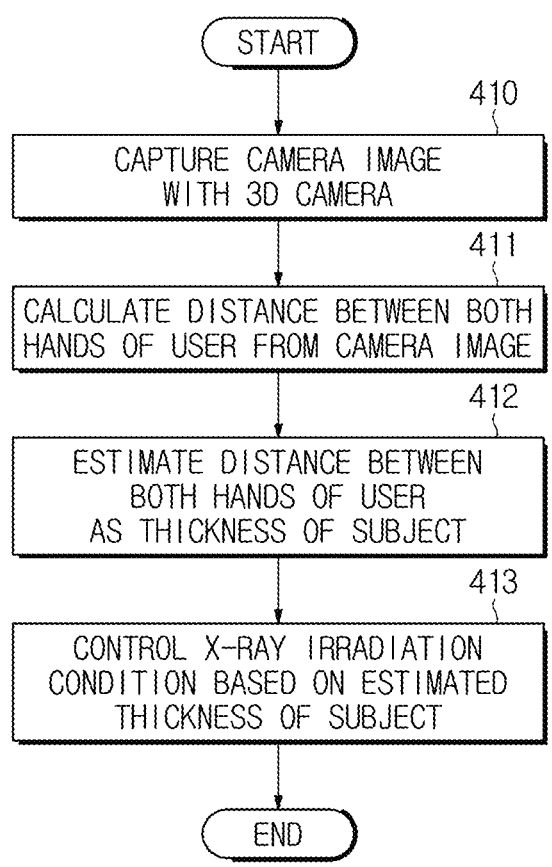
FIG. 11 is a flowchart illustrating a control method of an X-ray imaging apparatus, according to an embodiment of the present disclosure.

FIG. 11 is a flowchart illustrating a control method of an X-ray imaging apparatus, according to an embodiment of the present disclosure.

Referring to FIG. 11, a camera image is captured using the photographing device 120, in 410. The photographing device 120 may include a 3D camera for acquiring depth information of a subject. Turning back to FIGS. 6 and 7, the user places one hand $H_L$ in front of the X-raying portion of the subject P while placing the other hand $H_R$ at the same point as the X-ray detector 200 on the Y-axis. For example, the distance between the hand $H_L$ placed in front of the X-raying portion and the X-ray detector 200 is equal to the distance between the hand $H_L$ and the other hand $H_R$.

A distance between the hands of the user is calculated from a camera image, in 411. Since the photographing device 120 includes the 3D camera that may acquire depth information of an object appearing in the camera image, the controller 140 may obtain depth information of each of the hands $H_L$, $H_R$ appearing in the camera image. The depth information as herein used may refer to a distance between the photographing device 120 and either hand $H_L$, $H_R$. Specifically, the controller 140 uses an object recognition algorithm to recognize each of the hands $H_L$, $H_R$ appearing in the camera image and calculates the depth of either hand $H_L$, $H_R$. The controller 140 may obtain the distance between the hands $H_L$, $H_R$ appearing in the camera image from the difference in thickness between the hand $H_L$ placed in front of the X-raying portion and the hand $H_R$ placed in the back of the X-raying portion.

The distance between the hands of the user is estimated as thickness of the subject, in 412, and based on the estimated thickness of the subject, X-ray irradiation condition is controlled, in 413. The thickness of the subject refers to the thickness of the X-raying portion. The X-ray irradiation condition may vary by thickness D of the X-raying portion. Accordingly, the controller 140 may control the X-ray irradiation condition based on the thickness information obtained from the camera image and the X-ray irradiation conditions by the X-raying portion may be stored in the storage 170 in advance. The X-ray irradiation condition may include at least one of exposure parameters, such as a tube voltage (Kvp), a tube current (mA), exposure time (s), a filter type and thickness, a target material of anode, focal spot size, etc., and scatter parameters, such as a grid angle or center position, field of view (FOV), etc.

Figure 12:
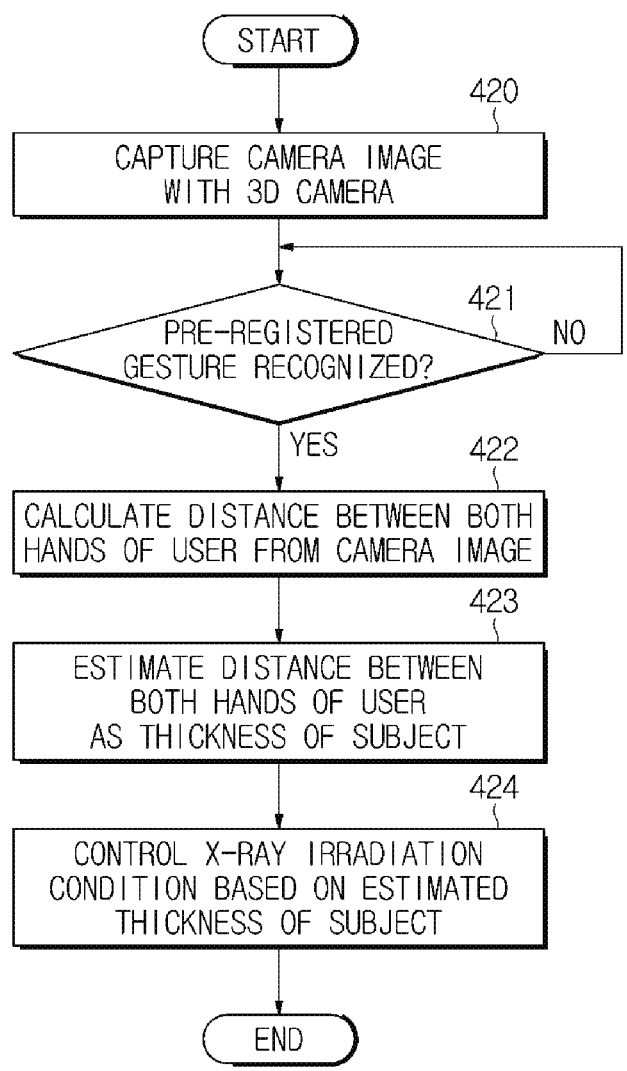
FIG. 12 is a flowchart illustrating how to measure the thickness of a subject if a preset event occurs in a control method of an X-ray imaging apparatus, according to an embodiment of the present disclosure.

FIG. 12 is a flowchart illustrating how to measure the thickness of an object if a preset event occurs in a control method of an X-ray imaging apparatus, according to an embodiment of the present disclosure.

Referring to FIG. 12, a camera image is captured using a 3D camera, in 420. The photographing device 120 including the 3D camera may have been taking camera images before the hands $H_L$, $H_R$ of the user are placed a distance of the thickness D of the subject away from each other. For example, the user may manipulate the input 152 from when beginning preparing for X-ray imaging and enter a command to capture a camera image, and the photographing device 120 may start taking a moving image according to the command.

If a preset event occurs during the capturing of a camera image, the thickness D information of the subject may be obtained by using a camera image captured at the point when the event occurs.

Recognition of a pre-registered gesture may be set in advance as an event to measure the thickness of the subject.

Accordingly, the controller 140 analyzes the camera image to determine whether a pre-registered gesture is recognized, in 421. Turning back to FIG. 8, if the user makes a pre-registered gesture with one hand $H_L$ after placing the hands $H_L$, $H_R$ a distance of the thickness D of the subject away from each other, the controller 140 may determine that a preset event has occurred. Specifically, the controller 140 may recognize the user's hand appearing in the camera image by means of an object recognition algorithm and recognize a gesture made by the user's hand using a gesture recognition algorithm. If the recognized gesture corresponds to the pre-registered gesture, it is considered that an event to measure the thickness D of the subject has occurred.

When the pre-registered gesture is recognized in 421, a distance between the hands of the user is calculated from the camera image, in 422, and the distance between the hands of the user is estimated as the thickness of the subject, in 423. For example, the controller 140 may control the photographing device 120 to capture a still image at the point when the event occurs, and calculate the distance between the hands from the captured still image.

The X-ray irradiation condition is controlled based on the estimated thickness of the subject, in 424, and X-raying is performed.

Figure 13:
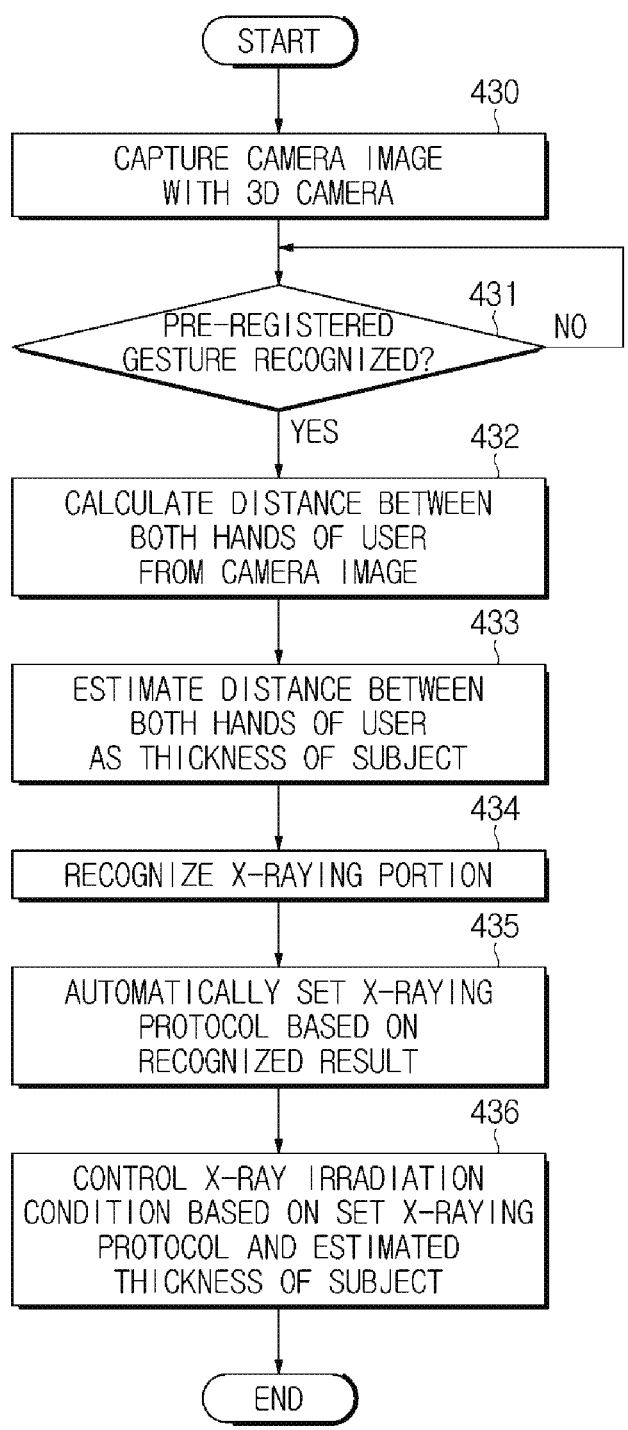
FIG. 13 is a flowchart illustrating how to automatically recognize a portion to be X-rayed using a camera image in a control method of an X-ray imaging apparatus, according to an embodiment of the present disclosure.

FIG. 13 is a flowchart illustrating how to automatically recognize a portion to be X-rayed using a camera image in a control method of an X-ray imaging apparatus, according to an embodiment of the present disclosure.

Referring to FIG. 13, a camera image is captured using a 3D camera, in 430.

The controller 140 analyzes the camera image to determine whether a pre-registered gesture is recognized, in 431.

When the pre-registered gesture is recognized in 431, a distance between the hands of the user is calculated from the camera image, in 432, and the distance between the hands of the user is estimated as the thickness of the subject, in 433.

An X-raying portion is recognized from the camera image, in 434. The controller 140 may apply an object recognition algorithm to recognize the X-raying portion from the camera image. In this regard, the controller 140 may recognize a portion where there are the user's hands $H_L$, $H_R$ as an X-raying portion.

Based on the result of recognition, an X-raying protocol may be automatically set, in 435.

The X-ray irradiation condition is controlled based on the set X-raying protocol and the estimated thickness of the subject, in 436, and X-raying is performed. Information about the X-ray irradiation condition based on the thickness of the X-raying portion and the X-raying protocol may be stored in the storage 170 in advance.

Figure 14:
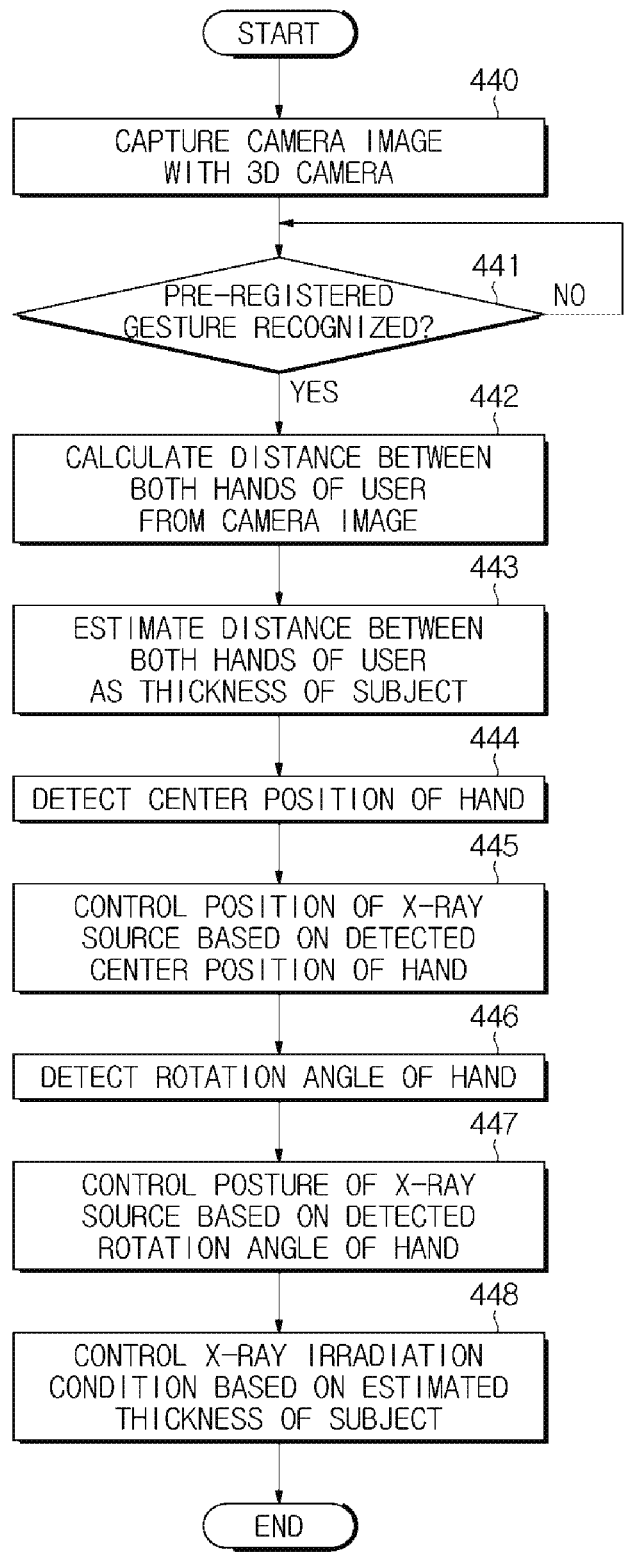
FIG. 14 is a flowchart illustrating how to control a position and posture of an X-ray source using a camera image in a control method of an X-ray imaging apparatus, according to an embodiment of the present disclosure.

FIG. 14 is a flowchart illustrating how to control a position and posture of an X-ray source using a camera image in a control method of an X-ray imaging apparatus, according to an embodiment of the present disclosure.

Referring to FIG. 14, a camera image is captured using a 3D camera, in 440.

The controller 140 analyzes the camera image to determine whether a pre-registered gesture is recognized, in 441.

When the pre-registered gesture is recognized in 441, a distance between the hands of the user is calculated from the camera image, in 442, and the distance between the hands of the user is estimated as the thickness of the subject, in 443.

The controller 140 may recognize the hand H of the user from the camera image and detect a position of the center Hc of the recognized hand H, in 444. Since the photographing device 120 includes a 3D camera, the position of the hand's center Hc may be calculated in 3D space coordinates.

The position of the X-ray source is controlled based on the detected center position of the hand, in 445. The controller 140 may calculate an amount of control to correspond the position of the X-ray tube to the position of the hand's center Hc based on the relationship between the camera coordinate system and a global coordinate system and a relative position of the X-ray tube and the photographing device 120. The controller 140 may send a control signal corresponding to the calculated amount of control to the source driver 130 to control the position of the X-ray source 110 by moving or rotating the moving carriage 40, the post frame 50, or the rotary joint 60.

The controller 140 detects a rotation angle of the user's hand from the camera image, in 446. An angle of the hand placed in front or back of the X-raying portion may correspond to the angle of the X-raying portion. The angle as herein used refers to an angle from the ground. The controller 140 may detect an angle of the hand H from the camera image including the 3D information.

The position of the X-ray source is controlled based on the detected rotation angle of the hand, in 447. The controller 140 may calculate an amount of control to correspond the posture of the X-ray source 110 to the detected angle. The controller 140 may control a rotation angle of the X-ray source 110 in the fourth direction D4 or in the fifth D5 direction by sending a control signal corresponding to the calculated amount of control to the source driver 130 and rotating the rotary joint 60.

The X-ray irradiation condition is controlled based on the estimated thickness of the subject, in 448, and X-raying is performed.

The control method of an X-ray imaging apparatus in an embodiment is not restricted to a sequence of thickness calculation of the X-raying portion, recognition of the X-raying portion, and control of the position and posture of the X-ray source 110.

With the X-ray imaging apparatus and control method thereof in accordance with the aforementioned embodiment, information about an X-raying portion, information about the thickness of the X-raying portion, information about the position to be X-rayed, information about an X-raying angle, or the like, which is required in setting an X-ray irradiation condition, may be obtained by using the user's hand appearing in the camera image without using an extra marker, thereby easily obtaining more accurate information at low costs.

According to an X-ray imaging apparatus and control method thereof in accordance with embodiments of the present disclosure, a hand of the user may be photographed, and from the photographed image, information about a thickness of a subject, information about a photographed spot or information about a photographing angle may be easily obtained.

Several embodiments have been described, but a person of ordinary skill in the art will understand and appreciate that various modifications can be made without departing the scope of the present disclosure. Thus, it will be apparent to those ordinary skilled in the art that the disclosure is not limited to the embodiments described, but can encompass not only the appended claims but the equivalents. The scope of the present disclosure should be interpreted by the accompanying claims and the equivalents should also be interpreted as falling within the scope of the present disclosure.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An X-ray imaging apparatus comprising:
   an X-ray source configured to generate and irradiate an X-ray;
   a photographing device equipped in the X-ray source and configured to capture a camera image; and
   a controller configured to:
      detect a plurality of indicators from the camera image,
      calculate a thickness of an X-raying portion of a subject based on a distance between the plurality of indicators, wherein the indicators are different objects from the subject, and
      control an X-ray irradiation condition based on the thickness of the X-raying portion,
   wherein the photographing device comprises a three dimensional (3D) camera which obtains a depth information, and
   wherein the distance between the plurality of indicators corresponds to a difference in position between the plurality of indicators in an irradiation direction of the X-ray determined based on the depth information.

2. The X-ray imaging apparatus of claim 1, wherein the plurality of indicators comprises both hands of a user.

3. The X-ray imaging apparatus of claim 2, wherein, in the camera image, one of the hands of the user is located in front of the X-raying portion of the subject and the other of the hands of the user located a distance of the thickness of the X-raying portion away from the one of the hands of the user.

4. The X-ray imaging apparatus of claim 2, wherein the controller is configured to calculate a distance between the hands using a camera image captured at a point when a preset event occurs if the preset event occurs.

5. The X-ray imaging apparatus of claim 4, wherein the controller is configured to determine that the preset event has occurred based on recognizing that at least one of the hands makes a pre-registered gesture.

6. The X-ray imaging apparatus of claim 4, wherein the controller is configured to recognize the X-raying portion of the subject from the camera image and set an X-raying protocol based on the recognized X-raying portion.

7. The X-ray imaging apparatus of claim 6, wherein the controller is configured to recognize a portion where at least one of the hands of the user is located in the camera image as the X-raying portion.

8. The X-ray imaging apparatus of claim 6, wherein the controller is configured to control the X-ray irradiation condition based on the calculated distance between the hands and the set X-raying protocol.

9. The X-ray imaging apparatus of claim 2, wherein the controller is configured to detect a center position of at least one of the hands of the user in the camera image and move the X-ray source to a position corresponding to the center position.

10. The X-ray imaging apparatus of claim 9, wherein the controller is configured to detect an angle of at least one of the hands of the user in the camera image and control an angle of the X-ray source to correspond to the angle of the at least one of the hands of the user.

11. The X-ray imaging apparatus of claim 1, wherein the X-ray irradiation condition comprises at least one of a tube voltage, a tube current, an exposure time, a filter type, filter thickness, a target material of anode, a focal size, a grid angle of a grid, a center position of the grid, and a field of view (FOV).

12. The X-ray imaging apparatus of claim 1, wherein the controller is configured to detect the plurality of indicators in the camera image when performing X-raying in a portable mode.

13. A control method of an X-ray imaging apparatus, the method comprising:
 capturing a camera image using a photographing device equipped in an X-ray source;
 detecting a plurality of indicators in the camera image;
 calculating a thickness of an X-raying portion of a subject based on a distance between the plurality of indicators, wherein the indicators are different objects from the subject; and
 controlling an X-ray irradiation condition based on the thickness of the X-raying portion,
 wherein the photographing device comprises a three dimensional (3D) camera which obtains a depth information, and
 wherein the distance between the plurality of indicators corresponds to a difference in position between the plurality of indicators in an irradiation direction of the X-ray determined based on the depth information.

14. The method of claim 13, wherein the plurality of indicators comprises both hands of a user.

15. The method of claim 14, wherein, in camera image, one of the hands of the user located is in front of the X-raying portion of the subject and the other of the hands of the user is located a distance of the thickness of the X-raying portion away from the one of the hands of the user.

16. The method of claim 14, further comprising:
 determining whether a preset event occurs; and
 calculating a distance between the hands using a camera image captured at a point when the preset event occurs if the preset event occurs.

17. The method of claim 16, wherein determining whether a preset event occurs comprises determining that the preset event has occurred based on recognizing that at least one of the hands makes a pre-registered gesture.

18. The method of claim 14, further comprising:
 detecting at least one of a center position of at least one of the hands of the user in the camera image; and
 moving the X-ray source to a position corresponding to the center position.

* * * * *